(12) United States Patent
Yamasaki et al.

(10) Patent No.: US 6,585,787 B2
(45) Date of Patent: Jul. 1, 2003

(54) CERIUM BASED ABRASIVE MATERIAL

(75) Inventors: Hidehiko Yamasaki, Tokyo (JP); Yoshitsugu Uchino, Tokyo (JP); Kazuaki Takahashi, Saitama (JP)

(73) Assignee: Mitsui Mining & Smelting Co., Ltd., Tokyo (JP)

( * ) Notice: Subject to any disclaimer, the term of this patent is extended or adjusted under 35 U.S.C. 154(b) by 0 days.

(21) Appl. No.: 10/181,450

(22) PCT Filed: Dec. 12, 2001

(86) PCT No.: PCT/JP01/10879
§ 371 (c)(1),
(2), (4) Date: Jul. 18, 2002

(87) PCT Pub. No.: WO02/48280
PCT Pub. Date: Jun. 20, 2002

(65) Prior Publication Data
US 2003/0051412 A1 Mar. 20, 2003

(30) Foreign Application Priority Data
Dec. 13, 2000 (JP) .......................................... 2000-379179

(51) Int. Cl.[7] ........................... B24B 37/00; C09K 3/14; C01F 17/00
(52) U.S. Cl. ............................. 51/309; 51/307; 423/263
(58) Field of Search .................... 51/307, 309; 423/263

(56) References Cited
FOREIGN PATENT DOCUMENTS

| EP | 31749 | * | 7/1981 |
|---|---|---|---|
| EP | 153227 | | 8/1985 |
| EP | 239478 | | 9/1987 |
| JP | 09183966 | * | 7/1997 |
| JP | 11269455 | * | 10/1999 |
| JP | 2000-26840 | | 1/2000 |
| JP | 2000188270 | * | 7/2000 |

* cited by examiner

Primary Examiner—Michael Marcheschi
(74) Attorney, Agent, or Firm—Rothwell, Figg, Ernst & Manbeck, P.C.

(57) ABSTRACT

There is provided a cerium-based abrasive which enables formation of a highly accurate polished surface and has improved grindability. There is also provided a method of evaluating cerium-based abrasives in a relatively easy manner. In order to achieve the above objects, the cerium-based abrasive of this invention is a cerium-based abrasive containing 40% by weight or more of cerium oxide (on the basis of the total weight of rare earth oxides) which is characterized by further containing 0.5 to 10% by weight of fluorine per 100% by weight of the cerium-based abrasive, in terms of atomic weight, and polishing particles consisting of crystals with a lattice constant measured by an X-ray powder diffraction method ranging from 0.544 to 0.560 nm. And the method of evaluating cerium-based abrasives of this invention is a method including the steps of: analyzing samples of cerium-based abrasive to be subjected to evaluation by the X-ray powder diffraction method; obtaining a diffraction angle ($\theta$) of at least one of maximum peaks appearing over the prescribed four ranges; and calculating a lattice constant of crystals constituting the polishing particles of the cerium-based abrasive using the above diffraction angle ($\theta$).

1 Claim, 1 Drawing Sheet

● Cerium Oxide Type Crystal
▲ ROF (LaOF)

● Cerium Oxide Type Crystal
▲ ROF (LaOF)
■ Rare Earth Fluoride ($LaF_3$)

CERIUM BASED ABRASIVE MATERIAL

CROSS REFERENCE TO RELATED APPLICATION

This application is a National Phase Entry Application from PCT/JP01/10879 filed Dec. 12, 2001, and designating the U.S.

TECHNICAL FIELD

This invention relates to a method of evaluating cerium-based abrasives containing cerium oxide as a main ingredient, and to a cerium-based abrasive and a method of producing the same.

BACKGROUND ART

Cerium-based abrasives containing cerium oxide ($CeO_2$) as a main ingredient have been used for polishing a wide variety of glass materials, and in recent years they have been used particularly for polishing glass materials for use in electric and electronic equipment, for example, glass for magnetic recording media such as hard disks and glass substrates of liquid crystal display (LCD), and have found their application in a wider field.

The cerium-based abrasives are divided into two types: high-cerium abrasives (containing 70% or more cerium oxide) and low-cerium abrasives (containing roughly 50% cerium oxide), depending on the cerium oxide content in the total rare earth oxide content (hereinafter referred to as TREO for short); however, there is no major difference in production process between the above two types and the production is performed in the steps of: chemical treatment of the raw material (wet treatment), filtration, roasting after drying, grinding and classifying. As a raw material, a natural material, bastnasite concentrate produced by the ore dressing of rare earth ores called bastnasite, was often used; however, in recent years rare earth oxides or rare earth carbonates artificially synthesized from bastnasite ores or relatively inexpensive complex ores produced in China have come into wide use.

The reasons the cerium-based abrasives are in wide use are that the application of the cerium-based abrasives provides a polished surface of high accuracy, in addition, allows a large amount of glass materials to be polished and removed in a relatively short period of time because of their grindability. As for the polishing mechanism of the cerium-based abrasives, though there is no very clear fixed theory of it, it is considered that a fluorine component contained in the cerium-based abrasives plays an important role. Specifically, it is considered that the cerium-based abrasives have not only a mechanical polishing function, which abrasives generally have, due to the polishing particles consisting mainly of cerium oxide, but also a chemical polishing function such that the fluorine component contained in the cerium-based abrasives reacts with the glass surface and forms a fluoride, which promotes the attack on the glass surface.

As described above, the cerium-based abrasives exhibit their excellent polishing characteristics only when they can produce effects of both mechanical and chemical functions. And as for the criteria for the abrasive quality, the cerium-based abrasives are required to have the same qualities as those general abrasives are required to have; specifically, they are required to have polishing particles with a uniform particle diameter and contain no coarse particles which may cause scratches in the polished surface, and moreover, they are required to have a proper fluorine grade (concentration).

In the cerium-based abrasives of the prior art, their fluorine content, particle diameter of polishing particles, roasting temperature and classifying conditions have been all properly controlled and thereby excellent abrasives have been supplied.

However, in view of the future demand for cerium-based abrasives, it is natural to desire the development of more excellent abrasives than ever. In the technical fields of hard disks, glass substrates for LCD, etc. in particular, there have been demands for the hard disks and the glass substrates to have still higher recording density. In order to meet these demands, it is considered, abrasives are required which have such higher grindability that provides a highly accurate polished surface and moreover allows speeding up of a given amount of polishing.

As for the details of the abrasives' fluorine treatment, roasting temperature, classifying conditions, etc., they have often been determined empirically. However, the correlation among them are not always simple, and it is difficult to estimate the polishing characteristics of abrasives particularly on the basis of the record during the production process, such as roasting temperature and classifying conditions. Accordingly, the evaluation of the polishing characteristics of cerium-based abrasives has been carried out by taking the trouble to actually polish glass materials and then measuring the polished values and observing the presence of scratches having occurred in a polished surface; however, the polishing test in which glass materials are actually polished is troublesome. Furthermore, it is impossible to evaluate the polishing characteristics of cerium-based abrasives simply by their fluorine content. Thus, a simpler evaluation criterion for abrasives is desired to be established, and it is considered that such a simple criterion is required particularly when a new abrasive is made by way of trial by changing the raw materials and production conditions used from the conventional ones to new ones.

This invention has been made in the light of the above circumstances; accordingly, an object of this invention is to provide a cerium-based abrasive, which enables the formation of a highly accurate polished surface and has improved grindability, and a method of producing the same. Further, another object of this invention is to provide a method of evaluating cerium-based abrasives in a relatively simple manner.

DISCLOSURE OF THE INVENTION

In order to solve the aforementioned problems, the inventors have conducted an intensive investigation thereof, resulting in directing their attention to changes in crystal structure of cerium oxide due to the behavior of fluorine during the process of producing cerium-based abrasives, in particular before and after roasting. And the inventors have come to the conclusion that the crystal structures of polishing particles contained in a cerium-based abrasive having a cerium oxide content of 40% or more (on the TREO basis) are all the same when they have been formed into an abrasive, the processes of the crystallization differ depending on the raw materials, though.

The crystal structure of the polishing particles contained in the cerium-based abrasives produced from rare earth oxides as a raw material is as follows. Cerium oxide in the raw material state before undergoing roasting exists in the form of a cerium oxide type of cubic crystal of chemical formula: $Ce_xLn_yO_z$ (where Ln represents rare earth metal elements including cerium, and x, y and z are related to one another by the following equation: $2x \leq z \leq 2(x+y)$, hereinafter the cerium oxide type of cubic crystal shall be referred to as cerium oxide phase) where rare earth metals, such as La and Nd, exist in cerium crystal in the form of a solid solution. Fluorine in the raw material state before undergoing roasting combines with rare earth metals and exists in the form of a rare earth fluoride ($LnF_3$), and this rare earth fluoride exists in a single-phase state or in the cerium oxide phase in the form of a solid solution.

When this abrasive raw material is roasted, the rare earth fluoride existing in a single-phase state is oxidized and part of or the whole of the same is changed into LnOF, and at the same time, the rare earth fluoride existing in the cerium oxide phase in the form of a solid solution is liberated from the cerium oxide phase, oxidized, and tends to be changed into LnOF. Accordingly, the abrasive having undergone roasting consists of cerium oxide phase in which rare earth fluoride exists in the form of a solid solution (the amount of the rare earth fluoride in the form of a solid solution differs depending on the roasting temperature), LnOF, and rare earth fluoride.

On the other hand, for the crystal structure of the polishing particles contained in the cerium-based abrasives produced from bastnasite concentrate or rare earth carbonate as a raw material, since the raw material before undergoing roasting is considered to consist of rare earth fluoride carbonate, rare earth carbonate, rare earth fluoride, etc., the crystal structure in such a state differs from that of the cerium-based abrasives whose raw material is the rare earth oxide. The rare earth fluoride carbonate and the rare earth carbonate are, however, changed into cerium oxide type of crystal during the process of roasting, and their behavior after the roasting is the same as that of the rare earth oxide having undergone roasting. Thus oxidization and liberation of the rare earth fluoride occur, and the abrasive having undergone roasting consists of cerium oxide phase in which rare earth fluoride exists in the form of a solid solution, LnOF, and rare earth fluoride.

Then the inventors considered that the liberation of the rare earth fluoride during the prpcess of producing a cerium-based abrasive might bring about a change in structure of the cerium oxide phase, leading to decrease in crystal lattice of the cerium oxide phase and that there might be a certain correlation between the decrease in crystal lattice of the cerium oxide phase and the polished value of abrasive as well as the accuracy of the polished surface. And the inventors finally found that, for the abrasives exhibiting excellent polishing characteristics, the lattice constant is within a given range and the range is almost constant independent of the record during the production process, such as roasting temperature.

The factors influencing the polishing characteristics of the abrasives are not necessarily clear yet; however, the inventors have confirmed after their intensive investigation that in the abrasives having a large polished value, the LnOF phase grows, while in the abrasives in which a large amount of rare earth fluoride remains, occurrence of scratches is observed in the polished surface. Thus, it is considered that the polished value and the accuracy of the polished surface are influenced by the amount of the LnOF phase, in other words, the balance between the amount of the rare earth fluoride liberated from the aforementioned cerium oxide phase and the amount of the rare earth fluoride remaining as it is in the LnOF phase. It is also considered that the balance between the amount of the liberated rare earth fluoride and the amount of the remaining rare earth fluoride influences the lattice constant of the cerium oxide phase and there exists a preferred range, in terms of polishing characteristics, of the lattice constant of the cerium oxide phase contained in the abrasive.

On the other hand, it is considered that even if the lattice constant is within a prescribed range, the amounts of the LnOF phase and of the rare earth fluoride differ depending on the fluorine content. And as described above, the larger the amount of the LnOF phase becomes, the higher the polished value of the abrasive becomes, but on the other hand, if a large amount of the rare earth fluoride remains in the abrasive, scratches occur in the polished surface. Accordingly, it is considered that even in the abrasives whose lattice constant is within the above range, there exists a suitable fluorine content range only in which they can exhibit excellent polishing characteristics.

Thus the inventors concentrated their energies on the investigation of finding cerium-based abrasives which exhibit excellent polishing characteristics, on the basis of both lattice constant of the cerium oxide phase and fluorine content, and finally have made this invention.

The invention is a cerium-based abrasive containing 40% by weight or more of cerium oxide (per 100% of rare earth oxide) which further contains 0.5 to 10% by weight of fluorine per 100% of cerium-based abrasive, in terms of atomic weight, and polishing particles consisting of crystal with the lattice constant measured by the X-ray powder diffraction method ranging from 0.544 to 0.560 nm.

The reason for the lattice constant of the cerium oxide type of crystal to be limited to the range of 0.544 to 0.560 nm is that, according to the inventors' investigation, with the lattice constant less than 0.544 nm the polished value is increased, but scratches occur in the polished surface, whereas with the lattice constant more than 0.560 nm no scratches occur, but sufficient polished value cannot be obtained.

The fluorine content is preferably in the range of 0.5% by weight to 10% by weight. The reason for the fluorine content to be limited to the above range is that with the fluorine content more than 10% by weight rare earth fluoride which is a factor of causing scratches remains, resulting in occurrence of a large number of scratches during the polishing operation, whereas with the fluorine content less than 0.5% by weight sufficient polished value cannot be obtained because there exists no LnOF phase which is effective in polishing operation, the amount of the rare earth fluoride remaining is small, though.

The cerium-based abrasive according to this invention enables the efficient formation of a highly accurate polished surface as well as the polishing operation under excellent conditions of grindability. In the cerium-based abrasive according to this invention, the average particle diameter of the polishing particles is not limited to any specific ones.

In the method of producing the cerium-based abrasive according to this invention, in particular, in the method of regulating the fluorine content and the lattice constant to the aforementioned range, the fluorine content is regulated by carrying out the fluorine treatment of the raw material under adjusted conditions and the lattice constant is regulated by carrying out the roasting operation at adjusted temperature.

And as the materials for the cerium-based abrasives, there are two types: one utilizing natural raw materials such as bastnasite concentrate and the other utilizing artificial raw materials such as rare earth oxides and rare earth carbonates. The bastnasite concentrate as a natural raw material contains fluorine by nature; therefore, a fluorine component is added only if needed and the amount added is adjusted according to the fluorine content the bastnasite concentrate has by nature. On the other hand, rare earth oxides and rare earth carbonates, as artificial raw materials, in the raw material state contain no fluorine; therefore, a fluorine component is added thereto before entering the roasting step so as to give an intended fluorine concentration. The process of adding a fluorine component to the artificial raw materials uses fluorine-containing compounds, such as hydrofluoric acid, ammonium fluoride and ammonium hydrogenfluoride, or the aqueous solution thereof.

Where the fluorine content of a cerium-based abrasive is in the range of 0.5% by weight to 10% by weight, in order for the lattice constant of cerium oxide to fall in a prescribed range, the roasting temperature is preferably in the range of 700 to 1100° C. The reason is that with the roasting temperature lower than 700° C. the LnOF phase, which is effective in polishing operation, does not grow, giving a low polishing value. On the other hand, with the roasting temperature higher than 1100° C. the LnOF phase is considered to grow sufficiently, but abnormal grain growth occurs in cerium oxide, creating coarse polishing particles. The roasting temperature of 780° C. to 980° C. is particularly preferable.

As described so far, the fluorine content and lattice constant of a cerium-based abrasive and the polishing characteristics of the same are closely related to each other. Accordingly, it may be considered that the polishing characteristics of a cerium-based abrasive can be estimated by measuring its fluorine content and lattice constant. As for the fluorine content, there has been established a certain procedure for examining it and the examination has been carried out therewith; but on the other hand, there has been established no method of measuring the lattice constant of a cerium-based abrasive having a certain fluorine content and evaluating the polishing characteristics of the same.

Under such circumstances, the invention is also a method of evaluating cerium-based abrasives which includes the steps of: collecting samples of cerium-based abrasive to be subjected to evaluation; analyzing the collected samples of cerium-based abrasive by the X-ray powder diffraction method; and calculating the lattice constant of the crystals constituting the polishing particles of the cerium-based abrasive using the analytical values.

In obtaining an angle of diffraction which is to be the basis for the calculation of the lattice constant, the angle of diffraction ($^\theta$) of at least one of the maximum peaks appearing over the following four ranges shall be obtained.

(a) $2^\theta = A_1°$ to $A_2°$
(b) $2^\theta = B° \pm 3.0°$
(c) $2^\theta = C° \pm 3.0°$
(d) $2^\theta = D° \pm 3.0°$ wherein if the wave length of the X-ray used in the X-ray powder diffraction method is expressed by $\lambda$ (nm), then $A_1$, $A_2$, B, C and D can be shown by the following equations:

$$A_1 = 360 \div \pi \times \sin^{-1}(1.127174 \times \lambda)$$

$$A_2 = 360 \div \pi \times \sin^{-1}(3.245569 \times \lambda)$$

$$B = 360 \div \pi \times \sin^{-1}(1.843583 \times \lambda)$$

$$C = 360 \div \pi \times \sin^{-1}(2.588335 \times \lambda)$$

$$D = 360 \div \pi \times \sin^{-1}(3.047405 \times \lambda)$$

For example, where the incident X-ray is Cu $K_\alpha$ ray and the diffracted X-ray is obtained on the basis of the diffraction pattern produced by the Cu $K_{\alpha_1}$ ray ($\lambda = 0.1540562$ nm), these diffraction angle measuring ranges are as follows:

$A_1 = 20°$, $A_2 = 60°$, $B = 33.0°$, $C = 47.0°$ and $D = 56.0°$.

The reason for selecting the wave length of X-ray whose maximum peaks appear over the above four ranges is that X-ray diffraction analysis usually uses peaks which show a sufficient intensity and appear over as high angle ranges as possible and, for the cerium oxide type of crystal which is the object of this invention, the maximum peaks appearing over the above ranges satisfy such conditions. In calculating a lattice constant using the X-ray diffraction method just as does this invention, the angle of diffraction may be obtained by using only one of such peaks; however, to obtain as highly accurate a lattice constant as possible, it is preferable to obtain more than one angle of diffraction and use the obtained values for the calculation of the lattice constant by the least square method or the extrapolation method.

For the cerium-based abrasive of this invention, its cerium oxide content is 40% or more (on the TREO basis) and the cerium oxide phase contained in the abrasive is mostly cubic crystal, and the peaks appearing over the four ranges correspond to the following plane indices of cerium oxide type of cubic crystal.

(a) (1 1 1) plane
(b) (2 0 0) plane
(c) (2 2 0) plane
(d) (3 1 1) plane

According to this invention, the polishing characteristics of cerium-based abrasives can be evaluated by the lattice constant, the characteristic the abrasives themselves have. And since the X-ray powder diffraction method used for measuring the lattice constant is an easy analytical method which takes only a short time, the polishing characteristics of cerium-based abrasives can be evaluated easily without taking the trouble to conduct complicated polishing tests. This is very advantageous particularly when evaluating the polishing characteristics of cerium-based abrasives whose raw materials and production conditions are unknown or those of the cerium-based abrasives whose raw materials and production conditions are known, but which are new ones made by way of trial by modifying the conventional ones, and the use of the method makes the prediction as well as the evaluation of the polishing characteristics of cerium-based abrasives simpler and easier.

The X-ray powder diffraction method used as a method of analyzing the lattice constant of cerium-based abrasives is carried out in the ordinary manner. Specifically, the method is carried out in such a manner as to allow monochromatic X-ray to enter the collected sample of a cerium-based abrasive and measure the intensity of the scattered X-ray using, usually, an apparatus referred to as X-ray diffractometer. As a target in the X-ray diffraction analysis Cu, Mo, Fe, Co, W, Ag, etc. can be used, and the diffracted X-ray obtained by the $K_{\alpha_1}$ ray or $L_{\alpha_1}$ ray generated in the target is used in the calculation of lattice constant. The diffracted X-ray obtained by the $K_{\alpha_1}$ ray generated in the Cu target is particularly preferably applied. The intensity of the diffraction peaks by the X-ray of Fe etc. is low, which is likely to affect the accuracy of the lattice constant calculated. When using $K_{\alpha_1}$ ray, the X-ray with which the sample is irradiated may be either $K_\alpha$ ray or $K_{\alpha_1}$ ray alone; however, in the use of $K_\alpha$ ray the diffracted X-ray generated should be separated into that obtained by the $K_{\alpha_1}$ ray and that obtained by the $K_{\alpha_2}$ so that angles of diffraction are obtained on the basis of the diffracted X-ray obtained by the $K_{\alpha_1}$ ray. Preferably the measured values of the diffraction angle are first corrected using a standard reference material for high precision measurements (high purity silicon powder etc.) and then used for calculating lattice constant.

The calculation of lattice constant using the measured values of the diffraction angle ($^\theta$) is carried out as follows.

The relation between the diffraction angle ($\theta$) for a crystal plane measuredly the X-ray diffraction method and the lattice spacing (d) follows the following Bragg's equation:
[Mathematical Equation 1]

$$2d\sin\theta = \lambda$$

On the other hand, in the cubic crystal system, if the Miller indices of the crystal face of the cerium oxide type of crystal corresponding to the above diffraction angle are expressed by (h k l), then the following relation holds between the lattice spacing (d) and the lattice constant (a):
[Mathematical Equation 2]

$$\frac{1}{d^2} = \frac{h^2 + k^2 + l^2}{a^2}$$

Accordingly, the following relation should be established between the diffraction angle ($\theta$) and the lattice constant (a) from the mathematical equation 1 and the mathematical equation 2, and a lattice constant can be obtained from a certain diffraction.
[Mathematical Equation 3]

$$a = \frac{\lambda}{2\sin\theta}\sqrt{h^2 + k^2 + l^2}$$

For example, when obtaining the diffraction angle ($\theta$) at (111) plane, since h=k=l=1, the lattice constant can be shown by the following equation:
[Mathematical Equation 4]

$$a = \frac{\lambda}{2\sin\theta}\sqrt{3}$$

BEST MODE FOR CARRYING OUT THE INVENTION

In the following the preferred embodiments of this invention will be described together with a comparative example.
First Embodiment One kg of rare earth oxide containing 90% by weight of TREO which contains 70% by weight of cerium oxide was mixed with 1 l of water to prepare slurry, and the slurry was ground in a wet ball mill (of 5 l capacity) filled with steel balls 5 mm in diameter for 3 hours to give slurry consisting of powder with average particle diameter (micro track method D 50 (diameter of 50% accumulated particles)) of 1 μm. Three l of 1 mol/l ammonium fluoride solution was added to the slurry, and the slurry was washed with pure water and filtered to give a cake. Then the cake was dried, roasted at 920° C. for 3 hours, grounded again, and classified to give a cerium-based abrasive. The fluorine content of the cerium-based abrasive was 5.2%.

Figure 1:
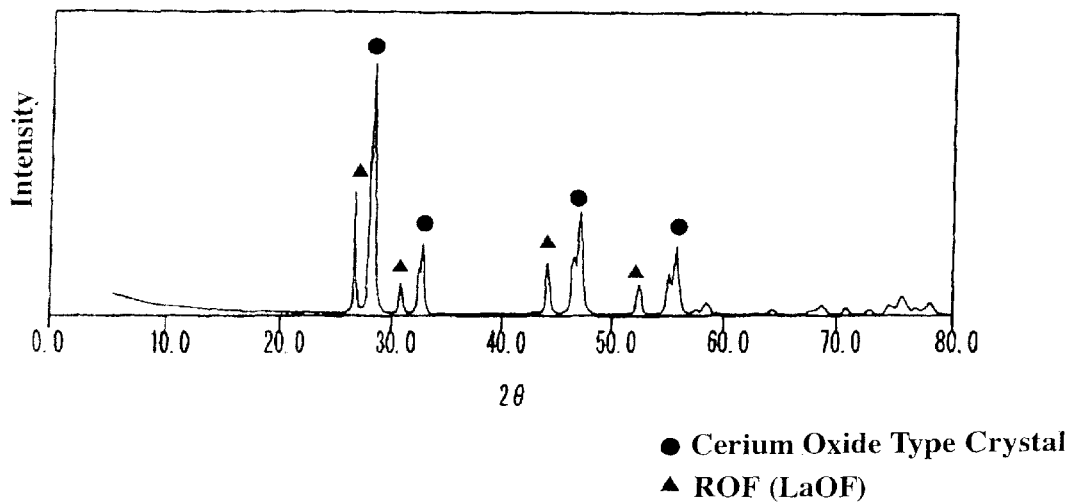
FIG. 1 is a graph showing the X-ray diffraction pattern of a cerium-based abrasive according to a first embodiment of this invention.

The cerium-based abrasive produced in the above steps was subjected to X-ray diffraction analysis to obtain the lattice constant of cerium oxide phase. A proper amount of the cerium-based abrasive of the first embodiment was sampled and uniformly filled into a sample holder so that the surface of the sample and the surface of the holder closely touched with each other, and the holder was installed in a X-ray diffractometer to obtain a X-ray diffraction pattern. The incident X-ray in this case was Cu $K_\alpha$ ray and the diffracted X-ray was on the basis of Cu $K_{\alpha_1}$ ray. The obtained X-ray diffraction pattern was compared with the reference peaks of various types of rare earth compounds, and the compounds shown by respective peaks were identified. FIG. 1 shows the X-ray diffraction pattern of the cerium-based abrasive produced according to this embodiment. In the same figure, in addition to the peaks of cerium oxide type of crystal ((111) plane) as main peaks, relatively high peaks of LaOF, which is the compound of lanthanum (La), as peaks of LnOF are observed. The lattice constant of cerium oxide obtained from the diffraction angle at the peak positions ($2\theta$) of the cerium oxide phase (111) was 0.546 nm.
Second to Sixth Embodiments Then five types of cerium-based abrasives were produced using as a raw material the same rare earth oxide as that of the first embodiment by grinding and drying the raw material in the same manner as the first embodiment while altering the amount of ammonium fluoride added and the roasting temperature. These five types of abrasives were subjected to X-ray diffraction analysis in the same manner as the first embodiment to calculate the lattice constant. The result is shown in Table 1.

TABLE 1

| Sample | Fluorine Concentration (%) | Roasting Temperature (° C.) | Crystal Lattice Constant (nm) |
|---|---|---|---|
| First Embodiment | 5.2 | 920 | 0.546 |
| Second Embodiment | 5.0 | 970 | 0.547 |
| Third Embodiment | 8.2 | 850 | 0.549 |
| Fourth Embodiment | 4.2 | 810 | 0.552 |
| Fifth Embodiment | 4.7 | 810 | 0.553 |
| Sixth Embodiment | 1.1 | 900 | 0.558 |

Comparative Example 1

As a comparative example to the first embodiment, a cerium-based abrasive with a lattice constant different from that of the first embodiment was produced using the same raw material as that of the first embodiment, and the produced cerium-based abrasive was subjected to X-ray diffraction. The cerium-based abrasive was obtained by grinding the same rare earth oxide as that of the first embodiment, adding 4.5 l of 1 mol/l ammonium fluoride solution and roasting at 990° C. The fluorine content of this cerium-based abrasive was 7.8%.

Figure 2:
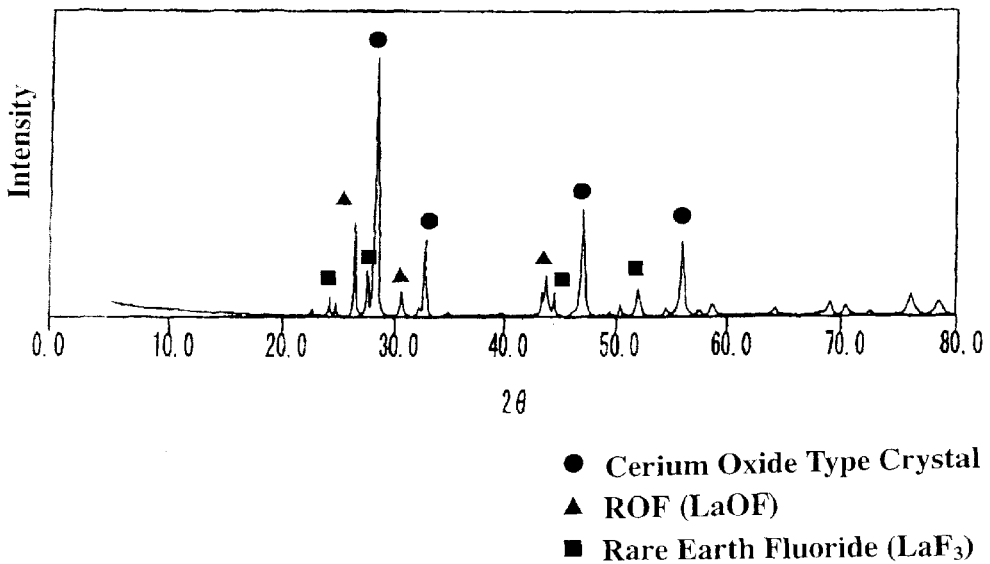
FIG. 2 is a graph showing the X-ray diffraction pattern of a cerium-based abrasive according to Comparative Example 1 of this invention.

When measuring the X-ray diffraction pattern of the comparative example 1, a pattern shown in FIG. 2 was obtained. In the X-ray diffraction pattern of this comparative example, in addition to the peaks of cerium oxide and LaOF which are also observed in FIG. 1, peaks of lanthanum fluoride ($LaF_3$) are observed. The lattice constant of the cerium oxide phase obtained was 0.543 nm.
Comparative Example 2 to 4

Three types of cerium-based abrasives were produced by altering the amount of ammonium fluoride added and the roasting temperature. These three types of abrasives were subjected to X-ray diffraction analysis to calculate the lattice constant. The results are shown in Table 2.

TABLE 2

| Sample | Fluorine Concentration (%) | Roasting Temperature (° C.) | Crystal Lattice Constant (nm) |
|---|---|---|---|
| Comparative Example 1 | 7.8 | 990 | 0.543 |
| Comparative Example 2 | 5.0 | 770 | 0.562 |
| Comparative Example 3 | 0.1 | 900 | 0.555 |
| Comparative Example 4 | 13.2 | 850 | 0.547 |

After polishing a glass material using the cerium-based abrasives according to the first to sixth embodiments and comparative examples 1 to 4, the polished values were measured and the state of the polished surfaces were compared and evaluated. First, each abrasive was dispersed in water to prepare 15% by weight abrasive slurry. This slurry was constantly stirred with a stirrer while the polishing test was conducted so that the abrasive would not precipitate.

Polishing of a glass material was conducted using a high speed polisher as a testing machine, borosilicate glass (BK7) of 65 mmϕ as a subject material to be polished, and a polyurethane polishing pad. The polishing conditions were such that abrasive slurry with slurry concentration of 15% by weight was supplied at a rate of 5 l/min, the pressure against the surface to be polished was set at 2.9 MPa (30 $kg/cm^2$), the rotation speed of the polisher was 3000 rpm, and the polishing duration was 1 minute. The glass material having been subjected to polishing was washed with pure water, followed by drying in a dust-free state.

The measurement of polished values in this evaluation test was conducted by measuring the weight of the glass before and after polishing to obtain the weight loss due to the polishing, and the polished values were expressed with the values obtained by converting the weight loss into thickness. The surface finish of the polished surface was evaluated on the basis of the presence of scratches on the polished surface and the presence of the abrasive particles remaining on the same. Specifically, the surface of the glass having been subjected to polishing was irradiated with halogen lamp of 300000 lx and observed by the transmission method and the reflection method. In this case, the evaluation of scratches was conducted by grading the scratches according to their number and size by deducting points out of 100. The evaluation results are shown in Table 3.

TABLE 3

| Sample | Fluorine Concentration (%) | Crystal Lattice Constant (nm) | Evaluation of Polishing Transmission | Evaluation of Polishing Reflection | Polished Value ($\mu$m) |
|---|---|---|---|---|---|
| First Embodiment | 5.2 | 0.546 | 100 | 97.0 | 35.7 |
| Second Embodiment | 5.0 | 0.547 | 100 | 97.0 | 34.6 |
| Third Embodiment | 8.2 | 0.549 | 100 | 98.0 | 32.1 |
| Fourth Embodiment | 4.2 | 0.552 | 100 | 97.0 | 27.2 |
| Fifth Embodiment | 4.7 | 0.553 | 100 | 95.5 | 26.0 |
| Sixth Embodiment | 1.1 | 0.558 | 100 | 100 | 20.2 |
| Comparative Example 1 | 7.8 | 0.543 | 80 | More scratches | 39.5 |
| Comparative Example 2 | 5.0 | 0.562 | 100 | 93 | 14.4 |
| Comparative Example 3 | 0.1 | 0.555 | 100 | 95 | 16.0 |
| Comparative Example 4 | 13.2 | 0.547 | 75 | More scratches | 33.4 |

It can be considered from the above results that the polished value decreases with the increase of the lattice constant and the polished value 25 $\mu$m or more cannot be obtained with the abrasive having a lattice constant 0.558 nm or more (sixth embodiment). The abrasive having a lattice constant 0.546 nm (first embodiment) shows the highest polished value, and in actuality the conditions of its polished surface were satisfactory.

As for the abrasives according to the comparative examples 1 and 2, both their fluorine contents were in the range of 0.5 to 10% by weight. In the comparative example 1, however, though its lattice constant was as relatively small as 0.543 nm and its polished value was high, occurrence of scratches was observed on the polished surface. In the comparative example 2, though its lattice constant was as relatively large as 0.562 nm and only a few scratches were observed on the polished surface, sufficient polished value could not be obtained. As for the abrasives according to the comparative examples 3 and 4, both their lattice constants were in the range of 0.544 to 0.560 nm. In the abrasive with a low fluorine content (comparative example 3), though occurrence of scratches was not observed, the polished value was small, whereas in the abrasive with a high fluorine content (comparative example 4), occurrence of scratches was observed.

The differences among the first to sixth embodiments and the comparative examples 1 to 4 described above may be attributed to the amount of LaOF contained in the abrasives. And the amount of LaOF is considered to influence the magnitude of the polished values. Further, in the comparative example 1, peaks of lanthanum fluoride were observed in its X-ray diffraction analysis, and it is considered from the observation that lanthanum fluoride remaining in the abrasive of the comparative example 1 was the chief factor in causing scratches on the polished surface.

Industrial Applicability

The invention has excellent grindability and enables the formation of a highly accurate polished surface, because the fluorine content of the invention and the lattice constant of cerium oxide contained in the same are regulated to 0.5 to 10% by weight and 0.544 to 0.560 nm, respectively.

The invention also enables the evaluation and quality control of the polishing characteristics of cerium-based abrasives in a shorter period time and in an efficient manner just by measuring the lattice constant of the cerium oxide phase contained in the abrasives. The use of this invention requires no polishing tests and makes easier the prediction as well as the evaluation of the polishing characteristics of cerium-based abrasives, particularly when the prediction and evaluation are conducted for the polishing characteristics of cerium-based abrasives whose raw materials and production conditions are unknown, or those of the cerium-based abrasives whose raw materials and production conditions are known, but which are new ones made by way of trial by modifying the conventional ones.

The cerium-based abrasive according to this invention has excellent grindability and enables the formation of highly accurate polished surface; therefore, it can be used, of course, for polishing a wide variety of glass materials, and it can be particularly suitably used for polishing the surfaces to be polished which the electric and electronic equipment has, for example, the surfaces of the glass for magnetic recording medium such as hard disks and those of the glass substrate of liquid crystal display (LCD). And the method of evaluating cerium-based abrasives according to this invention is the most suitable for the evaluation and quality control of the polishing characteristics of the cerium-based abrasive of this invention which are conducted in the production of the same.

What is claimed is:

1. A cerium abrasive comprising 40% by weight or more of cerium oxide (on the basis of a total weight of rare earth oxides), wherein said cerium abrasive contains 0.5 to 10% by weight of fluorine per 100% by weight of cerium abrasive, in terms of atomic weight, and the abrasive consist of crystals with a lattice constant measured by an X-ray powder diffraction method ranging from 0.544 to 0.560 nm.

* * * * *